United States Patent [19]
Heinicke et al.

[11] Patent Number: 5,834,024
[45] Date of Patent: Nov. 10, 1998

[54] CONTROLLED ABSORPTION DILTIAZEM PHARMACEUTICAL FORMULATION

[75] Inventors: Grant Wayne Heinicke, Fairview Park; Angelo Lepore, Magill; Angelo Mario Morella, Campbelltown, all of Australia

[73] Assignee: FH Faulding & Co. Limited, Parkside, Australia

[21] Appl. No.: 814,602

[22] Filed: Mar. 10, 1997

Related U.S. Application Data

[63] Continuation-in-part of Ser. No. 369,100, Jan. 5, 1995, abandoned.

[51] Int. Cl.[6] .................................................... A61K 9/54
[52] U.S. Cl. ......................... 424/497; 424/457; 424/458; 424/459; 424/461; 424/462; 424/490; 424/494
[58] Field of Search .......................... 424/451, 457, 424/458, 459, 461, 462, 463, 464, 468, 473, 474, 475, 480, 482, 489, 490, 494, 495, 496, 497; 514/964

[56] References Cited

U.S. PATENT DOCUMENTS

| | | | |
|---|---|---|---|
| 3,607,364 | 9/1971 | Lopez et al. | 427/2.2 |
| 3,835,221 | 9/1974 | Fulberth et al. | 424/458 |
| 4,496,558 | 1/1985 | DeMarinis et al. | 514/213 |
| 4,610,870 | 9/1986 | Jain et al. | 424/19 |
| 4,721,619 | 1/1988 | Panoz et al. | 424/459 |
| 4,828,840 | 5/1989 | Sakamoto et al. | 424/474 |
| 4,891,230 | 1/1990 | Geoghegan et al. | 424/461 |
| 4,894,240 | 1/1990 | Geoghegan et al. | 424/497 |
| 4,904,476 | 2/1990 | Mehta et al. | 424/456 |
| 4,917,899 | 4/1990 | Geoghegan et al. | 424/461 |
| 4,960,596 | 10/1990 | Debrageas et al. | 424/458 |
| 5,000,962 | 3/1991 | Sangekar et al. | 424/482 |
| 5,002,776 | 3/1991 | Geoghegan et al. | 424/497 |
| 5,133,974 | 7/1992 | Paradissis et al. | 424/480 |
| 5,137,733 | 8/1992 | Noda et al. | 424/497 |
| 5,149,542 | 9/1992 | Valducci | 424/493 |
| 5,202,128 | 4/1993 | Morella et al. | 424/469 |
| 5,219,621 | 6/1993 | Geoghegan et al. | 424/462 |
| 5,229,131 | 7/1993 | Amidon et al. | 424/451 |
| 5,229,135 | 7/1993 | Philippon et al. | 424/494 |
| 5,252,337 | 10/1993 | Powell | 424/456 |
| 5,254,347 | 10/1993 | Samejima et al. | 424/495 |
| 5,286,497 | 2/1994 | Hendrickson et al. | 424/490 |
| 5,336,504 | 8/1994 | Geoghagen et al. | 424/462 |
| 5,344,657 | 9/1994 | Desmolin | 424/458 |
| 5,364,620 | 11/1994 | Geoghagen et al. | 424/497 |
| 5,376,384 | 12/1994 | Eichel et al. | 424/480 |
| 5,439,689 | 8/1995 | Hendrickson et al. | |

FOREIGN PATENT DOCUMENTS

| | | |
|---|---|---|
| A-11969/88 | 8/1988 | Australia . |
| B-27077/88 | 6/1989 | Australia . |
| 3922 167 A1 | 1/1991 | Denmark . |
| 315 197 A1 | 5/1989 | European Pat. Off. . |
| 502 642 A1 | 9/1992 | European Pat. Off. . |
| 527 637 A1 | 2/1993 | European Pat. Off. . |
| 605 174 A1 | 7/1994 | European Pat. Off. . |

(List continued on next page.)

*Primary Examiner*—Jose' G. Dees
*Assistant Examiner*—Robert H. Harrison
*Attorney, Agent, or Firm*—E. Brendan Magrab

[57] ABSTRACT

A controlled absorption diltiazem pellet formulation for oral administration comprises a core having diltiazem or a pharmaceutically acceptable salt thereof as the active ingredient. The core is surrounded by a coating which has only a single layer which is comprised of a relatively major proportion of talc and relatively minor proportion of sodium lauryl sulfate admixed with a minor proportion of a pharmaceutically acceptable film-forming, first polymer permeable to water and diltiazem, and a major proportion of a pharmaceutically acceptable film-forming, second polymer that is less permeable to water and diltiazem than the first polymer. The core and the coating layer both exclude organic acids. The composition of the coating layer as well as the proportion of core to coating layer are effective to permit release of the diltiazem allowing controlled absorption following oral administration. By combining short lag and long lag pellets into a single formulation, the release of diltiazem is controlled over a twenty four hour period.

6 Claims, 5 Drawing Sheets

FOREIGN PATENT DOCUMENTS

| | | |
|---|---|---|
| 2 039 737 | 12/1979 | United Kingdom . |
| PCT/SE90/ 00500 | 2/1991 | WIPO . |
| PCT/GB91/ 01824 | 4/1992 | WIPO . |
| PCT/US92/ 04267 | 11/1992 | WIPO . |
| PCT/CA92/ 00290 | 1/1993 | WIPO . |
| PCT/FR92/ 01083 | 5/1993 | WIPO . |
| 94/28882 | 12/1994 | WIPO . |

CONTROLLED ABSORPTION DILTIAZEM PHARMACEUTICAL FORMULATION

CROSS REFERENCES TO RELATED APPLICATIONS

This application is a continuation-in-part of application Ser. No. 08/369,100 filed Jan. 5, 1995, now abandoned.

FIELD OF THE INVENTION

The present invention relates to controlled absorption pharmaceutical formulations and, in particular, to controlled absorption forms of diltiazem for once a day oral administration.

BACKGROUND OF THE INVENTION

Diltiazem, which is cis-(+)-3-(acetyloxy)-5-[2-(dimethylamino)ethyl]-2,3-dihydro- 2-(4-methoxyphenyl)-1,5-benzothiazepin-4(5H)-one, referred to herein as "diltiazem", is a benzothiazine derivative possessing calcium antagonist activity. Diltiazem blocks the influx of calcium ions in smooth and cardiac muscle and thus exerts potent cardiovascular effects. Diltiazem has been shown to be useful in alleviating symptoms of chronic heart disease, particularly angina pectoris and myocardial ischemia and hypertension, while displaying a low incidence of side effects. Diltiazem is available as diltiazem hydrochloride in tablet form in strengths of 30, 60, 90 and 120 mg. and in capsule form in strengths of 60, 90, 120, 180, 240 and 300 mg. Diltiazem is also available in injectable form with a strength of 5 mg./ml.

Diltiazem therapy typically starts with 30 mg. administered 4 times daily. The dosage is gradually increased to 180 to 360 mg./day, given in divided doses three or four times daily, at one- to two- day intervals until an optimum response is obtained. Diltiazem is extensively metabolized by the liver. According to professional use information issued by Marion Merrell Dow Inc., diltiazem in CARDIZEM® brand tablets is absorbed to about 80% and is subject to an extensive first-pass effect, giving an absolute bioavailability, compared to intravenous administration, of about 40%. Single oral doses of 30 to 120 mg. of CARDIZEM® diltiazem tablets result in peak plasma levels two to three hours after administration. Detectable plasma levels occur within 30 to 60 minutes after administration indicating that CARDIZEM® diltiazem tablets are readily absorbed. The plasma elimination half-life following single or multiple administration is approximately 3.5 hours. Therapeutic blood levels of CARDIZEM® diltiazem tablets appear to be in the range of 50 to 200 ng./ml.

Although conventional diltiazem tablets are administered three or four times daily, such frequent drug administration may reduce patient compliance and produce irregular blood levels. Consequently, adverse therapeutic effects can arise. There is therefore a need for a diltiazem formulation that ensures that diltiazem blood levels remain relatively stable over long periods of time without the need for frequent drug administration.

U.S. Pat. Nos. 4,721,619, 4,891,230, 4,917,899 and 5,219,621 disclose diltiazem formulations that purport to require administration once every twelve hours (i.e., twice a day). U.S. Pat. Nos. 4,894,240 and 5,002,776 disclose diltiazem formulations that purport to require administration once every 24 hours (i.e., once a day). To obtain the dissolution profiles disclosed in these patents, the formulations disclosed require a multi-layer membrane that coats the central core and an organic acid in the active core and/or in the multi-layer membrane. Suitable organic acids disclosed in these patents are adipic acid, ascorbic acid, citric acid, fumaric acid, malic acid, succinic acid and tartaric acid. According to professional use information issued by Marion Merrell Dow Inc., the CARDIZEM® CD diltiazem capsule is a sustained release diltiazem capsule containing 120, 180, 240 or 300 mg. diltiazem hydrochloride with a suggested dosage of one capsule a day. Similarly, to obtain a 24-hour diltiazem release profile, the pellets in the CARDIZEM® CD diltiazem capsule include fumaric acid, an organic acid, and a multi-layer membrane that coats the central core. According to the aforementioned patents, the pellets must be dried for a number of hours during and after the coating process. This procedure increases the manufacturing cost of such pellets. Additionally, the organic acid included in such formulations may have an irritating effect. Accordingly, a need exists for a sustained release diltiazem formulation for once a day administration which does not have an irritating effect and which also has a satisfactory dissolution rate.

SUMMARY OF THE INVENTION

The controlled absorption diltiazem pellet formulation for once a day oral administration of the present invention comprises a mixture of long and short lag pellets, each having a core with diltiazem or a pharmaceutically acceptable salt thereof as the active ingredient. The core is substantially free of an organic acid, i.e., the amount of such organic acid, if any, is sufficiently small so as not to substantially affect the release rate of the drum from the core. The core and has a coating which has only a single layer which is comprised of a mixture of a relatively large proportion of a lubricant and a relatively small proportion of a wetting agent in admixture with a minor proportion of a pharmaceutically acceptable film-forming, first polymer that is permeable to water and diltiazem, and a major proportion of a pharmaceutically acceptable film-forming, second polymer that is less permeable to water and diltiazem than the first polymer. As mentioned, the core and the coating layer of the pellets are substantially free of organic acids. The composition of the coating layer is effective to permit release of the diltiazem allowing controlled absorption over a twenty four hour period following oral administration.

The core of the pellets is preferably comprised of a central sphere of an inert ingredient, preferably a sugar sphere, diltiazem hydrochloride and a pharmaceutical binder, preferably hydroxypropyl cellulose.

The film-forming polymers in the coating layer are preferably cationic polymers synthesized from acrylic and methacrylic acid esters with a low content of quaternary ammonium groups, known as EUDRAGIT RL and EUDRAGIT RS. The wetting agent, preferably sodium lauryl sulfate, and the lubricant, preferably talc, as well as an optional plasticizing agent, preferably triethyl citrate, are also included in the coating layer.

By varying the proportion of the coating relative to the core, pellets with different dissolution profiles are obtained. Thus, by using cores of the same size and by increasing the thickness of the coating, the dissolution profile changes, even though the compositions of the core and the coating layer remain the same.

When measured in a type 2 dissolution apparatus (paddle) according to the U.S. Pharmacopoeia XXII in 0.1N HCl at 100 r.p.m. and at 37° C., a short lag pellet formulation exhibits the following dissolution profile: from 0% to 25% of the total diltiazem is released after 2 hours, from 30% to 100% of the total diltiazem is released after 4 hours, from 60% to 100% of the total diltiazem is released after 6 hours, from 80% to 100% of the total diltiazem is released after 8 hours, and from 90% to 100% of the total diltiazem is released after 13 hours.

When measured in a type 2 dissolution apparatus (paddle) according to the U.S. Pharmacopoeia XXII in 0.1N HCl at 100 r.p.m. and at 37° C., a long lag pellet formulation exhibits the following dissolution profile: from 0% to 10% of the total diltiazem is released after 2 hours, from 0% to 10% of the total diltiazem is released after 4 hours, from 0% to 15% of the total diltiazem is released after 6 hours, from 0% to 15% of the total diltiazem is released after 8 hours, from 60% to 100% is released after 18 hours and from 90% to 100% of the total diltiazem is released after 24 hours.

By encapsulating a mixture of these two types of pellets, and measuring in a type 2 dissolution apparatus (paddle) in 0.1N HCl at 100 r.p.m. and at 37° C., a once a day controlled release diltiazem capsule formulation exhibits the following dissolution profile is obtained: from 0% to 30% of the total diltiazem is released after 2 hours, from 0% to 50% of the total diltiazem is released after 4 hours, from 20% to 60% of the total diltiazem is released after 6 hours, from 30% to 70% of the total diltiazem is released after 8 hours, from 30% to 100% of the total diltiazem is released after 13 hours, and from 80% to 100% of the total diltiazem is released after 24 hours.

When a preferred embodiment, having a long lag to short lag pellet ratio of 60:40, is measured in a type 2 dissolution apparatus (paddle) in 0.1N HCl at 100 r.p.m. and at 37° C., the following dissolution profile is obtained: not more than 10% of the total diltiazem is released after 1 hour, from 20% to 45% of the total diltiazem is released after 6 hours, from 35% to 45% of the total diltiazem is released after 8 hours, from 35% to 45% of the total diltiazem is released after 11 hours, not less than 85% of the total diltiazem is released after 18 hours, and not less than 90% of the total diltiazem is released after 24 hours.

The short lag pellet of this preferred embodiment will typically exhibit the following in vitro dissolution profile: not more than 10% of the total diltiazem is released after 1 hour, 50% of the total diltiazem is released between 3 and 4½ hours, and not less than 85% of the total diltiazem is released after 8 hours. The long lag pellet of this preferred embodiment will typically exhibit the following in vitro dissolution profile: not more than 5% of the total diltiazem is released after 1 hour, 50% of the total diltiazem is released between 12 and 16 hours, and not less than 85% of the total diltiazem is released after 18 hours.

DETAILED DESCRIPTION OF THE PRESENTLY PREFERRED EMBODIMENTS

Figure 1:
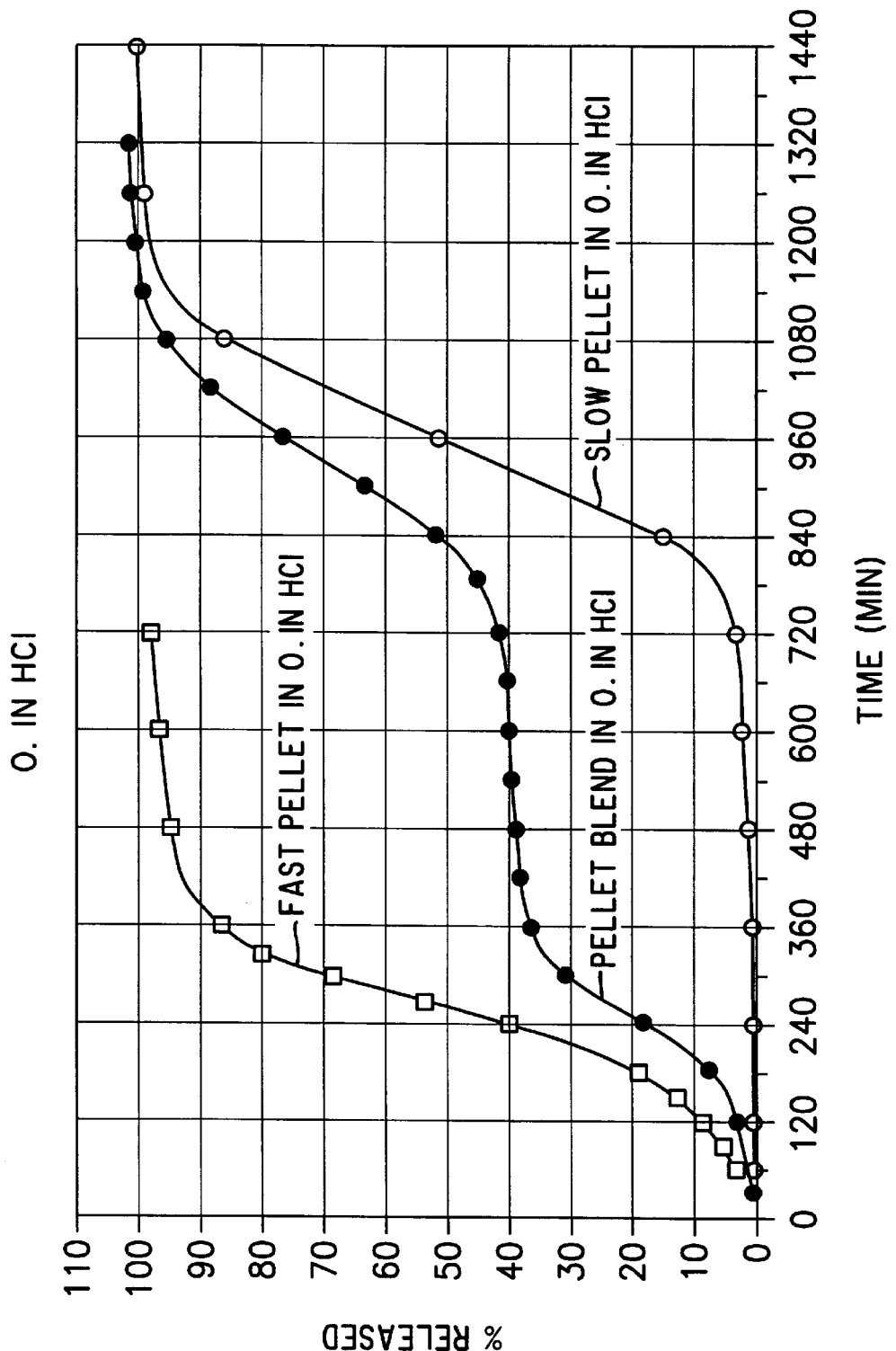
FIG. 1 is a graphical representation of percent dissolution against time in hours for the short lag pellets, the long lag pellets, and the blend containing such short lag pellets and long lag pellets prepared in accordance with Example 1, at pH 1.0.

The present invention provides a once a day diltiazem formulation for oral administration comprised of a tablet or capsule filled with pellets containing diltiazem. A mixture of two types of pellets is utilized, one in which the diltiazem is released into the bloodstream of a human subject soon after administration and one in which the diltiazem is released after a delay of approximately over 6 hours. As a result, the amount of diltiazem in the human subject remains relatively constant after onset over a 24 hour period after administration.

The pellets are comprised of a central core containing the active ingredient and a single coating layer covering the core.

The active core is preferably comprised of a central sphere, bead or seed of an inert ingredient, a pharmaceutically acceptable diltiazem containing compound and a pharmaceutical binder, emulsifier or stabilizer. The central inert core is preferably comprised of a sugar or starch sphere having an average diameter of from about 0.5 mm. to about 1.5 mm. The pharmaceutically acceptable diltiazem containing compound is preferably in the form of a pharmaceutically acceptable salt thereof, more particularly the hydrochloride salt thereof, diltiazem hydrochloride. The pharmaceutical binder is preferably hydroxypropyl cellulose, although other suitable known binders may be used, such as, for example, acacia, carboxymethylcellulose sodium, dextrin, ethylcellulose, gelatin, glucose, guar gum, hydroxyethyl cellulose, hydroxypropyl methylcellulose, methylcellulose, polymethacrylates, povidone, pregelatinized starch, sodium alginate, and zein, or a mixture of any two or more of the foregoing binders. No organic acids, such as adipic acid, ascorbic acid, citric acid, fumaric acid, malic acid, succinic acid, tartaric acid and fumaric acid, are required to be included in the core. The core may also include further components to those specified above such as a dispersing agent, glidant and/or surfactant.

The single coating layer is preferably comprised of a mixture of a relatively large proportion of a lubricant and a relatively small proportion of a wetting agent in admixture with a minor proportion of a first polymer that is permeable to diltiazem and water and a major proportion of a polymer that is less permeable to diltiazem and water than the first polymer. No organic acids, such as adipic acid, ascorbic acid, citric acid, fumaric acid, malic acid, succinic acid, tartaric acid and fumaric acid, are required to be included into the coating layer. A preferred permeable first polymer is the cationic polymer synthesized from acrylic and methacrylic acid ester with a low content of quaternary ammonium groups, known as EUDRAGIT RL manufactured by Röhm Pharma GmbH. In this compound, the ammonium groups give rise to the permeability of the polymer. The permeability of EUDRAGIT RL is reported as independent of pH. A preferred less permeable second polymer is another such cationic polymer known as EUDRAGIT RS manufactured by Röhm Pharma GmbH. EUDRAGIT RS is less permeable than EUDRAGIT RL because EUDRAGIT RS has fewer ammonium groups. The permeability of EUDRAGIT RS is reported to be also independent of pH.

Additional substances that can be used that are less permeable to diltiazem and water include ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or a mixture of any two or more of these. Suitable naturally occurring polymers or resins that are less permeable to water and diltiazem include shellac, chitosan, gumjuniper or a mixture of two or more of these.

The single coating layer may alternatively be comprised of a mixture of polymers, synthetic and/or naturally occurring, that are freely permeable, slightly permeable, water soluble, water insoluble, and polymers whose permeability and/or solubility is affected by pH. In addition to those referred to above, such suitable polymers for inclusion into the coating layer include EUDRAGIT S, EUDRAGIT L, EUDRAGIT E, polyvinyl alcohol and polyvinylpyrrolidone. Commercially available polymeric solutions and/or suspensions may also be used. These solutions/suspensions may optionally contain plasticizing agents to improve the polymer characteristics of the coating. Examples of such solutions and/or suspensions include EUDRAGIT RL 30D, EUDRAGIT L 30D, EUDRAGIT E 12.5, EUDRAGIT RL 12.5 P, EUDRAGIT RS 12.5, AQUACOAT made by FMC Corporation, and SURE-LEASE made by Colorcon Inc. AQUACOAT is an aqueous polymeric dispersion of ethylcellulose and contains sodium lauryl sulfate and cetyl alcohol. SURELEASE is an aqueous polymeric dispersion of ethylcellulose and contains dibutyl sebacate, oleic acid, ammoniated water and fumed silica.

In addition to the polymers, the coating layer includes a lubricant and a wetting agent. Preferably the lubricant is talc and the wetting agent is sodium lauryl sulfate.

Suitable alternatives for sodium lauryl sulfate may include agents such as acacia, benzalkonium chloride, cetomacrogol emulsifying wax, cetostearyl alcohol, cetyl alcohol, cholesterol, diethanolamine, docusate sodium, sodium stearate, emulsifying wax, glyceryl monostearate, hydroxypropyl cellulose, lanolin alcohols, lecithin, mineral oil, monoethanolamine, poloxamer, polyoxyethylene alkyl ethers, polyoxyethylene castor oil derivatives, polyoxyethylene sorbitan fatty acid esters, polyoxyethylene stearates, propylene glycol alginate, sorbitan esters, stearyl alcohol and triethanolamine, or a mixture of any two or more of the foregoing.

Suitable alternatives for talc that may be included in the coating are calcium stearate, colloidal silicon dioxide, glycerin, magnesium stearate, mineral oil, polyethylene glycol, and zinc stearate, aluminum stearate or a mixture of any two or more of the foregoing.

A plasticizing agent is preferably included in the coating to improve the elasticity and the stability of the polymer film and to prevent changes in the polymer permeability over prolonged storage. Such changes could affect the drug release rate. Suitable conventional plasticizing agents include acetylated monoglycerides, acetyltributylcitrate, acetyltriethyl citrate, castor oil, citric acid esters, dibutyl phthalate, dibutylsebacate, diethyloxalate, diethyl malate, diethylfumarate, diethylphthalate, diethylsuccinate, diethylmalonate, diethyltartarate, dimethylphthalate, glycerin, glycerol, glyceryl triacetate, glyceryltributyrate, mineral oil and lanolin alcohols, petrolatum and lanolin alcohols, phthalic acid esters, polyethylene glycols, propylene glycol, rape oil, sesame oil, triacetin, tributyl citrate, triethyl citrate, and triethyl acetyl citrate, or a mixture of any two or more of the foregoing. Triethyl citrate is the presently preferred plasticizing agent.

To the extent that naturally occurring oils and/or waxes can be used as part of the core and/or coating, these oils and waxes are substantially free of organic acids, i.e., the amount of such organic acid, if any, is sufficiently small so as not to substantially affect the release rate of the drug from the core.

Typically the core of the pellet comprises 60 to 80% of diltiazem hydrochloride as the active ingredient, 2 to 6% of hydroxypropyl cellulose and 18 to 34% of sugar, expressed as percentages of the total weight of the core. The coating layer of the pellet comprises 2 to 7% of a polymer of acrylic and methacrylic acid esters as the first polymer, 53 to 59% of a polymer of acrylic and methacrylic acid esters as the second polymer, 0 to 8 % of triethyl citrate, 0 to 8% of sodium lauryl sulfate, and 31 to 35% of talc, expressed as percentages of the total weight of the coating layer.

By varying the proportion of the coating in each pellet relative to the core, pellets with different dissolution profiles are obtained. Thus, by maintaining the size of the core and by decreasing or increasing the thickness of the coating, the dissolution profile of the resulting pellet is varied, even though the compositions of the core and the coating layer remain the same.

To form the active core, any suitable apparatus can be used and include a rotor granulator, pan coater, spheronizer and extruder. Preferably to form the active core, a slurry is made which includes ethanol, diltiazem and the binder. The slurry is then coated onto the central inert cores and the resultant active cores are then dried for about ¼ to about 2 hours at a temperature of from about 40° C. to about 60° C., preferably for about ½ hour at about 60° C.

To coat the active core, all of the coating ingredients except the lubricant are first dissolved in an ethanol solvent. The lubricant is then added to and/or suspended in the solution. The single coating layer is applied to the active cores using a WURSTER bottom spray coater until the desired coating thickness is obtained. The coated active cores, or pellets, are then dried for about ¼ to about 2 hours at a temperature of from about 30° C. to about 60° C., preferably for about ½ hour at 40° C., allowed to cool to ambient temperature, sieved through an appropriately sized mesh and dusted with talc.

Alternatively, the coating can be applied to the active cores using a conventional coating pan, an automated system such as a CF granulator, for example a FREUND CF granulator, a GLATT fluidized bed processor, an AEROMATIC, a modified ACCELA-COTA or any other suitably automated bead coating equipment.

The pellets may be filled into hard or soft gelatin capsules. The pellets may also be compressed into tablets using a binder and/or hardening agent commonly employed in tabletting such as microcrystalline cellulose sold under the trademark AVICEL or a co-crystallized powder of highly modified dextrins (3% by weight) and sucrose sold under the trademark DI-PAC in such a way that the specific dissolution rate of the pellets is maintained.

EXAMPLE 1

Short Lag Pellets:

Diltiazem hydrochloride (10.050 kg.) and hydroxypropyl cellulose (0.625 kg.) were mixed with ethanol (16.250 l) to form a homogeneous slurry. Sugar spheres (0.50 to 0.60 mm. in diameter) (5.000 kg.) were added into the rotor granulator and the slurry then applied. After approximately 2 hours, the active cores were dried for ½ hour at a temperature of 50° C.

To form the coating solution, EUDRAGIT RS (3.1 kg.), EUDRAGIT RL (0.22 kg.), triethyl citrate (0.33 kg.) and sodium lauryl sulfate (0.075 kg.) were dissolved in ethanol (24.4 l). Talc (1.86 kg.) was then added to the solution.

The single coating layer was applied to the active cores using a WURSTER bottom spray coater until an actual coat weight of about 12% based on the total pellet weight was obtained. The coated active cores were dried for about ½ hour at a temperature of about 40°, then cooled to ambient temperature, sieved through a 1400 μm mesh and dusted with talc.

The resulting short lag pellets had the following composition:

| Ingredient | Short Lag Pellets (per 100 g) | Weight % |
|---|---|---|
| Core: | | |
| diltiazem HCl | 56.3 g | 64.1% |
| hydroxypropyl cellulose | 3.5 g | 4.0 |
| sugar spheres | 28.0 g | 31.9 |
| Total | 87.8 g | 100.0% |
| Coating: | | |
| EUDRAGIT RL | 0.5 g | 4.1% |
| EUDRAGIT RS | 6.8 g | 55.3 |
| triethyl citrate | 0.7 g | 5.7 |
| sodium lauryl sulfate | 0.2 g | 1.6 |
| talc | 4.1 g | 33.3 |
| Total | 12.3 g | 100.0% |
| TOTAL (core + coating) | 100.1 g | |

Long Lag Pellets:

Diltiazem hydrochloride (10.050 kg.) and hydroxypropyl cellulose (0.625 kg.) were mixed with ethanol (16.250 l.) to form a homogeneous slurry. Sugar spheres (0.50 to 0.60 mm. in diameter) (5.000 kg.) were added into the rotor granulator and the slurry then applied. After approximately 2 hours, the active cores were removed and dried for ½ hour at a temperature of 50° C.

To form the coating solution, EUDRAGIT RS (11.4 kg.), EUDRAGIT RL (0.81 kg.), triethyl citrate (1.20 kg.) and sodium lauryl sulfate (0.275 kg.) were dissolved in ethanol (89.8 l.). Talc (6.82 kg.) was then added to the solution.

The single coating layer was applied to the active cores using a WURSTER bottom spray coater until an actual coat weight of about 29% based on total pellet weight was obtained. The coated active cores were dried for about ½ hour at a temperature of about 40° C., then cooled to ambient temperature, sieved through a 1400 μm mesh and dusted with talc.

The resulting long lag pellets had the following composition:

| Ingredient | Long Lag Pellets (per 100 g) | Weight % |
|---|---|---|
| Core: | | |
| diltiazem HCl | 44.7 g | 64.1% |
| hydroxypropyl cellulose | 2.8 g | 4.0 |
| sugar spheres | 22.2 g | 31.9 |
| Total | 69.7 g | 100.0% |
| Coating: | | |
| EUDRAGIT RL | 1.2 g | 4.0% |
| EUDRAGIT RS | 16.8 g | 55.4 |
| triethyl citrate | 1.8 g | 5.9 |
| sodium lauryl sulfate | 0.4 g | 1.3 |
| talc | 10.1 g | 33.3 |
| Total | 30.3 g | 99.9% |
| TOTAL (core + coating) | 100.0 g | |

Dissolution Test (pH 1.0) (pellets):

After the finished short lag and long lag pellets were dried to evaporate all solvents, the pellets were then subjected to a dissolution test. The dissolution rate of the pellets, 300 mg. diltiazem equivalent, was determined in a type 2 dissolution apparatus (paddle) according to the U.S. Pharmacopoeia XXII in 0.1N HCl at 100 r.p.m. in 900 ml. at 37° C. The diltiazem hydrochloride was quantitatively determined using U.V. spectrophotometry at 238 nm. The dissolution test was performed six times and the mean dissolution rate was as shown in FIG. 1 and below in Table 1:

TABLE 1

| Time (hours) | Short Lag Pellets (Mean % Diltiazem HCl Released) | Long Lag Pellets (Mean % Diltiazem HCl Released) |
|---|---|---|
| 1 | 3.2 | 0.3 |
| 2 | 8.5 | 0.4 |
| 3 | 18.9 | — |
| 4 | 39.6 | 0.5 |
| 5 | 68.2 | — |
| 6 | 86.3 | 0.7 |
| 7 | 92.4 | — |
| 8 | 94.7 | 0.9 |
| 10 | 96.7 | 1.3 |
| 12 | 97.8 | 3.1 |
| 14 | — | 14.5 |
| 16 | — | 51.0 |
| 18 | — | 86.5 |
| 21 | — | 99.2 |
| 24 | — | 100.3 |

By comparing the composition of the short lag pellets with that of the long lag pellets, it can be seen that the cores of the short lag pellets and the long lag pellets have the same relative proportions of ingredients. Similarly, the coating layers of the two types of pellets have the same relative proportions of ingredients. To generate different dissolution profiles, the proportion per pellet of the coating relative to the proportion of the core was changed. As can be seen from the data in Table 1, by maintaining the size of the core and by decreasing the thickness of the coating, a faster dissolution profile is obtained.

Dissolution Test (pH 1.0) (blend):

A mixture of the pellets described above was made comprising 40% short lag pellets and 60% long lag pellets (by drug weight content). A 300 mg. diltiazem equivalent of the mixture was subjected to a dissolution test. The dissolution rate of the capsule formulation was determined in a type 2 dissolution apparatus (paddle) according to the U.S. Pharmacopoeia XXII in 0.1N HCl at 100 r.p.m. in 900 ml. at 37° C. The diltiazem hydrochloride was quantitatively determined using U.V. spectrophotometry at 238 nm. The dissolution test was performed six times and the mean dissolution rate was as shown in FIG. 1 and below in Table 2:

TABLE 2

| Time (hours) | Blend Formulation (mean % diltiazem HCl released) |
| --- | --- |
| 1 | 1.3 |
| 2 | 2.9 |
| 4 | 18.1 |
| 6 | 36.2 |
| 8 | 38.7 |
| 10 | 39.7 |
| 12 | 41.5 |
| 14 | 51.4 |
| 16 | 76.3 |
| 18 | 95.1 |
| 20 | 100.4 |

Figure 4:
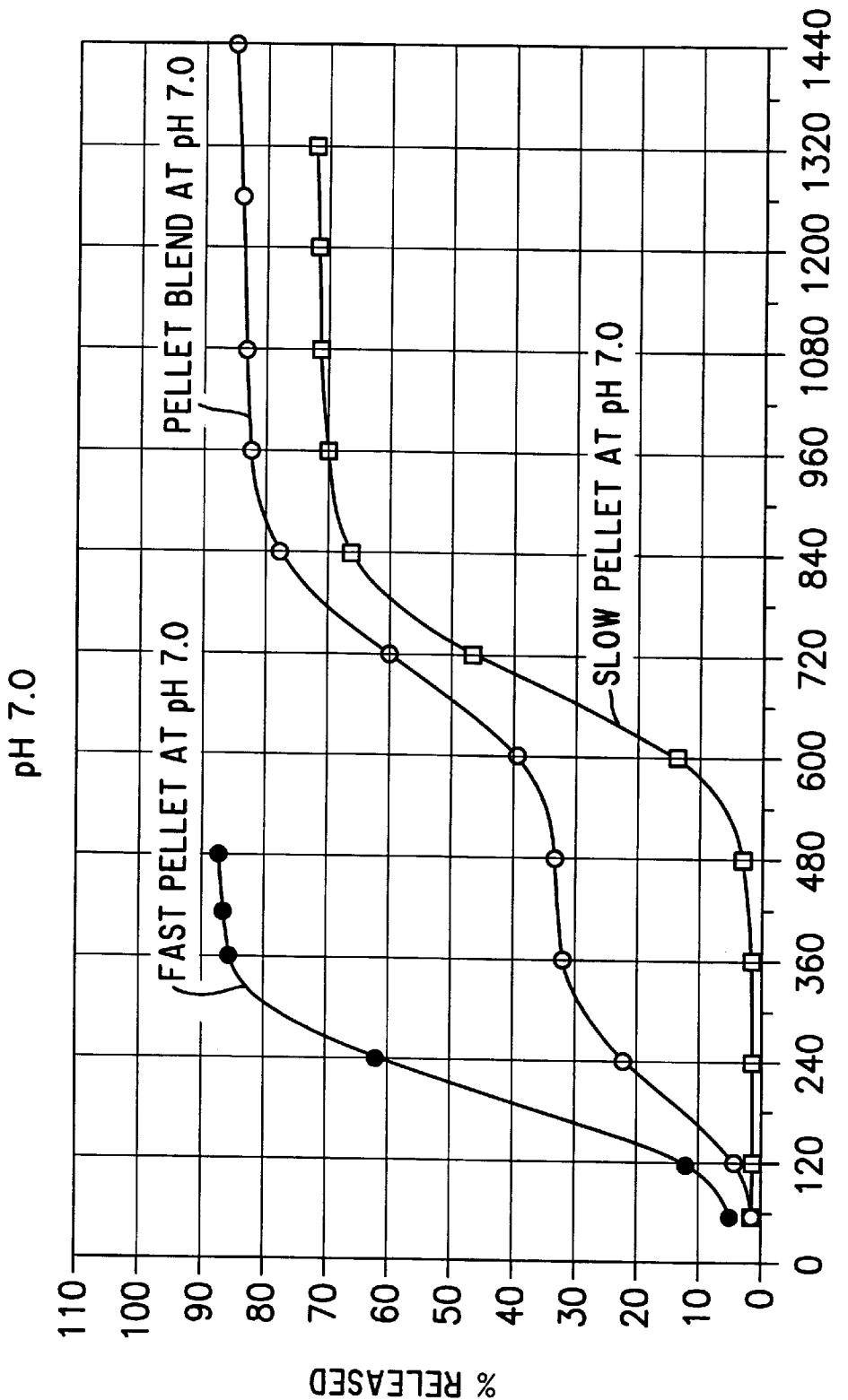
FIG. 4 is a graphical representation of percent dissolution against time in hours for the short lag pellets, the long lag pellets, and the blend containing such short lag pellets and long lag pellets prepared in accordance with Example 1, at pH 7.01.

Dissolution Test (pH 7.0) (pellets):

After the finished short and long lag pellets were dried to evaporate all solvents, the pellets were then subjected to a dissolution test. The dissolution rate of the pellets, 300 mg diltiazem equivalent, was determined in a type 2 dissolution apparatus (paddle) according to the U.S. Pharmacopoeia XXII at pH 7.0 using a phosphate buffer at 100 r.p.m. in 900 ml. at 37° C. The diltiazem hydrochloride was quantitatively determined using U.V. spectrophotometry at 238 nm. The dissolution test was performed three times and the mean dissolution rate was as shown in FIG. 4 and below in Table 3.

TABLE 3

| Time (hours) | Short Lag Pellets (mean % diltiazem HCl Released) | Long Lag Pellets (mean % diltiazem HCl Released) |
| --- | --- | --- |
| 1 | 4.9 | 1.4 |
| 2 | 11.8 | 1.4 |
| 4 | 61.7 | 1.5 |
| 6 | 85.6 | 1.5 |
| 8 | 87.4 | 2.9 |
| 10 | 88.2 | 13.7 |
| 12 | 89.0 | 46.4 |
| 14 | 89.6 | 66.1 |
| 16 | 90.4 | 70.5 |
| 18 | 90.9 | 71.5 |
| 21 | 92.0 | 72.1 (20 hrs) |
| 24 | 92.7 | 72.6 (22 hrs) |

Dissolution Test (pH 7.0) (blend)

A mixture of the pellets described above was made comprising 40% short lag pellets and 60% long lag pellets (by drug content weight). A 300 mg. diltiazem equivalent of the mixture was subjected to a dissolution test. The dissolution rate of the capsule formulation was determined in a type 2 dissolution apparatus (paddle) according to the U.S. Pharmacopoeia XXII at pH 7.0 using a phosphate buffer at 100 r.p.m. in 900 ml. at 37° C. The diltiazem hydrochloride was quantitatively determined using U.V. spectrophotometry at 238 nm. The dissolution test was performed three times and the mean dissolution rate was as shown in FIG. 4 and below in Table 4.

TABLE 4

| Time (hours) | Blend Formulation (mean % diltiazem HCl released) |
| --- | --- |
| 1 | 1.4 |
| 2 | 3.9 |
| 4 | 21.4 |
| 6 | 31.7 |
| 8 | 33.4 |
| 10 | 39.5 |
| 12 | 60.3 |
| 14 | 77.4 |
| 16 | 82.4 |
| 18 | 83.2 |
| 21 | 84.2 |
| 24 | 85.4 |

Comparative Dissolution Study

Figure 5:
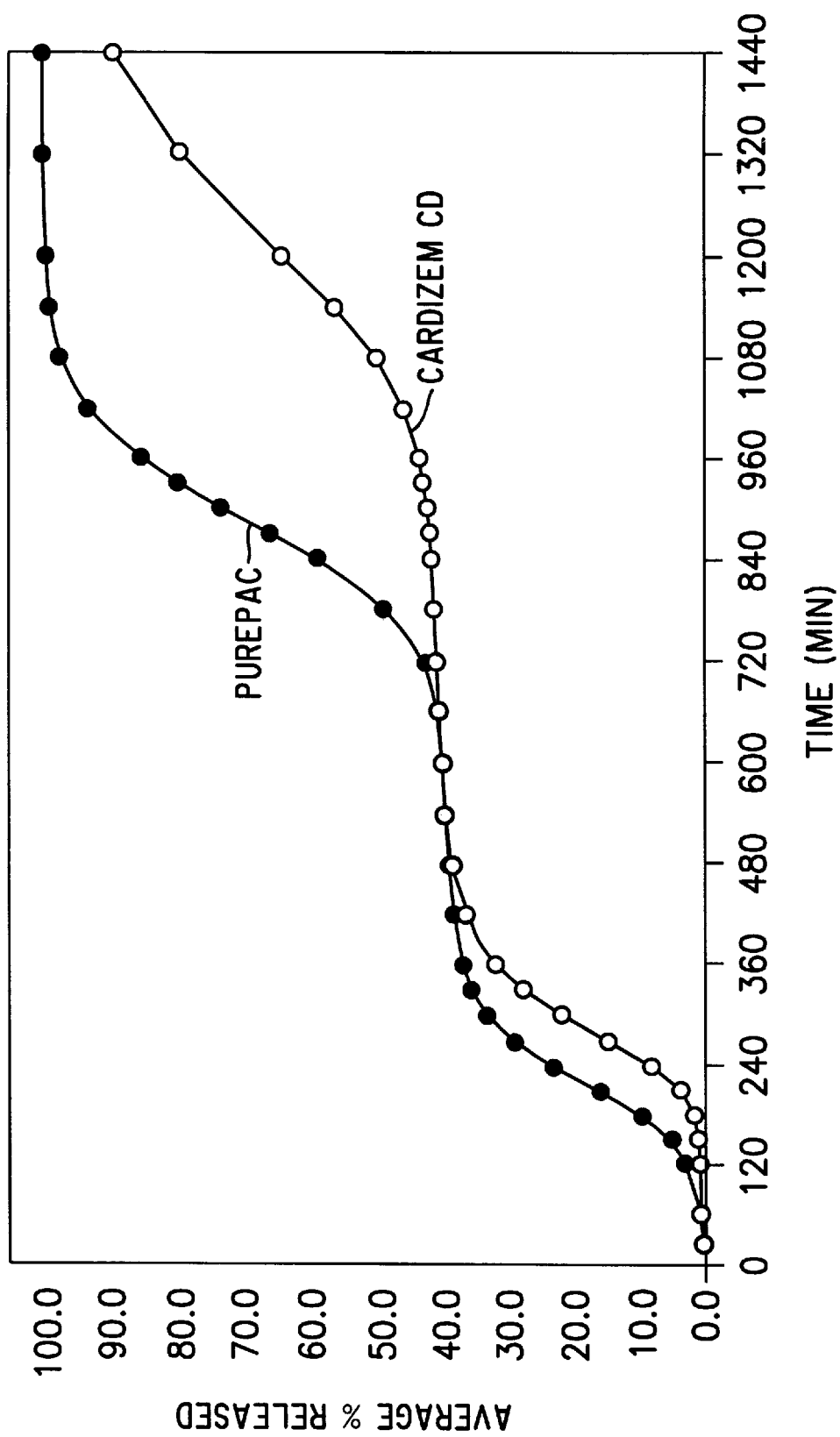
FIG. 5 is a graphical representation of percent dissolution against time in hours for the diltiazem capsule blend formulation prepared in Example 1 and for CARDIZEM® CD capsules, in 0.1N HCl.

A mixture of the pellets described above was made comprising 40% short lag pellets and 60% long lag pellets (by drug content weight). A 300 mg diltiazem equivalent of the encapsulated mixture was subjected to a dissolution test and compared to the reference product, CARDIZEM® CD, under the following conditions: apparatus 2 (paddle), 0.1N HCl, 100 r.p.m., 900 ml, 37° C. The diltiazem hydrochloride was quantitatively determined using U.V. spectrophotometry at 238 nm. The dissolution test was performed on 12 units (whole capsules) of both the test and reference product and the mean dissolution rate was as shown in FIG. 5 and below in Table 5.

TABLE 5

| Time (hours) | Diltiazem HCl ER Capsules, 300 mg (mean % diltiazem released) | CARDIZEM ® CD Capsules, 300 mg (mean % diltiazem released) |
| --- | --- | --- |
| 1 | 0.7 | 0.4 |
| 6 | 37.0 | 32.2 |
| 8 | 39.5 | 37.8 |
| 11 | 40.9 | 39.5 |
| 18 | 98.2 | 47.7 |
| 24 | 100.7 | 89.2 |

Figure 2:
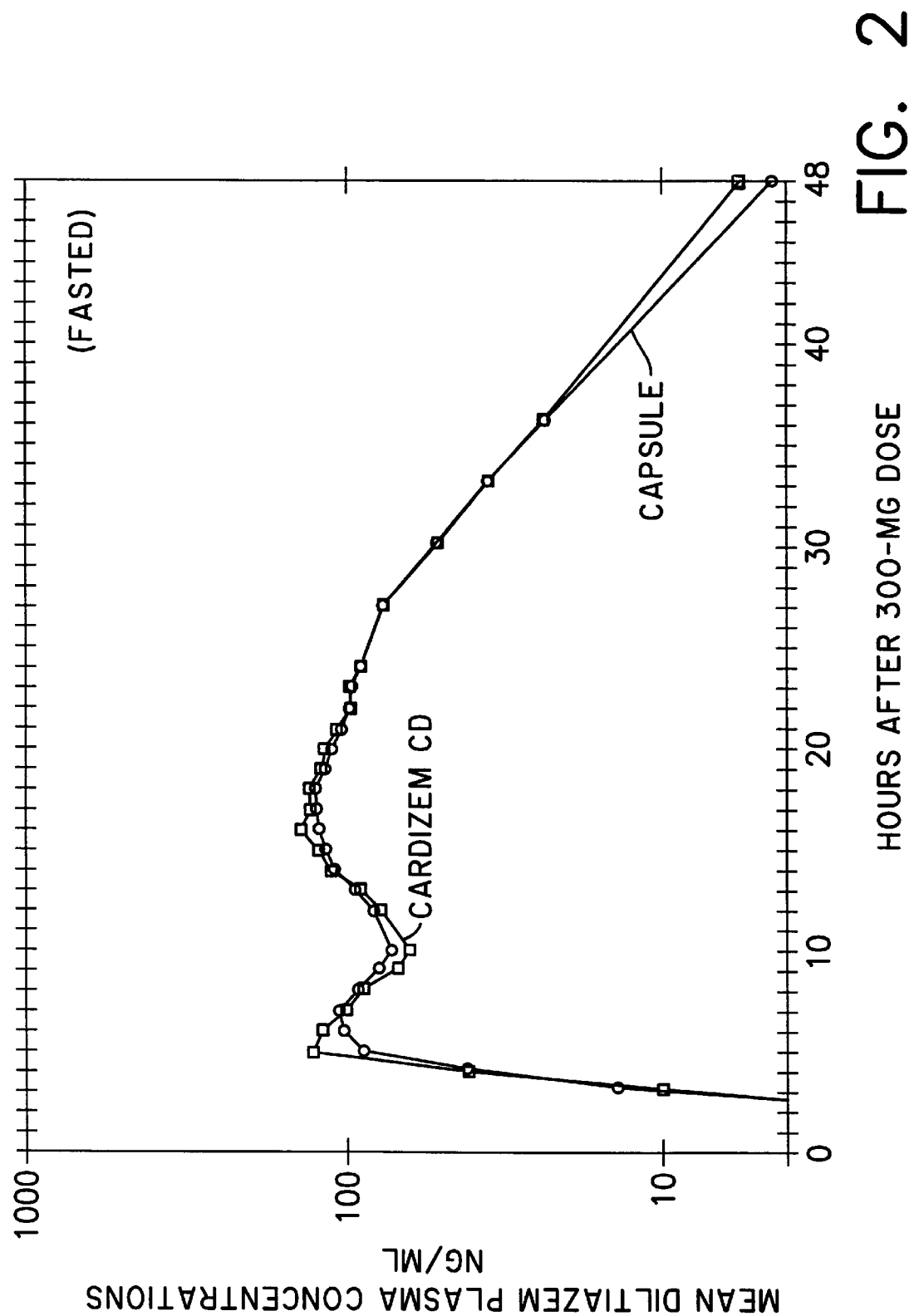
FIG. 2 is a graphical representation of plasma levels (ng/ml) of diltiazem against time (hours) after administration to fasted humans for the diltiazem capsule formulation prepared in Example 1 and for a CARDIZEM® CD diltiazem capsule.
Figure 3:
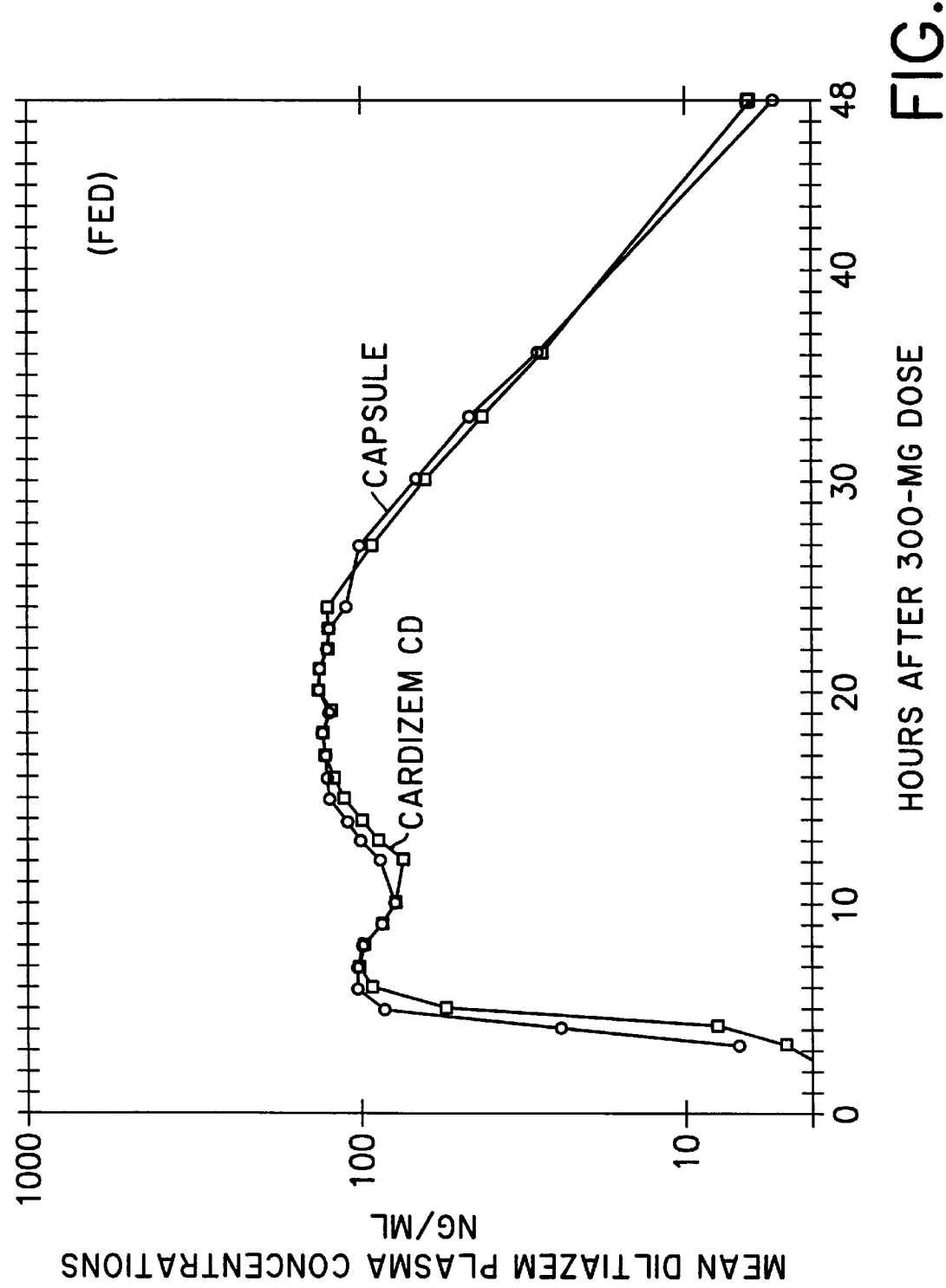
FIG. 3 is a graphical representation of plasma levels (ng/ml) of diltiazem against time (hours) after administration to fed humans for the diltiazem capsule formulation prepared in Example 1 and for a CARDIZEM® CD diltiazem capsule.

Pharmacokinetic Data:

Two, two-way, single dose crossover studies were performed simultaneously to assess the bioequivalence of the diltiazem capsule formulation (containing both short and long lag pellets) described above in Example 1 and CARDIZEM® CD diltiazem capsules when given under fasted and fed conditions. The effects of the Example 1 capsule formulation (40% short lag pellets and 60% long lag pellets) and the CARDIZEM® CD diltiazem capsule, each containing 300 mg. of diltiazem, were compared in 20 human healthy male subjects after an overnight fast, and in 8 subjects after a standard breakfast. Serial blood samples were collected from the subjects over 48 hours after each 300 mg. dose. A two-week washout separated the dosings. Nineteen of the fasted subjects and seven of the fed subjects completed the studies. Plasma samples from all of the subjects who completed the studies were analyzed using a validated chromatograph procedure and are shown in FIG. 2 (fasted subjects) and in FIG. 3 (fed subjects). In FIGS. 2 and 3, the curves denoted as "Capsule" refer to the diltiazem capsule formulation described in Example 1 above. The pharmacokinetic data for the subjects (n=19) who fasted prior to administration was as shown below in Table 5:

TABLE 5

| Parameter (fasted subjects) | Example 1 Diltiazem Capsule Formulation | CARDIZEM ® CD Capsule Formulation |
|---|---|---|
| $AUC_{0-48}$ (ng-hr/ml) | 2783.29 | 2899.47 |
| $AUC_{inf}$ (ng-hr/ml) | 2872.76 | 2974.07 |
| $C_{max1}$ (ng/ml) | 113.98 | 131.77 |
| $C_{max2}$ (ng/ml) | 138.42 | 140.62 |
| $C_{max}$ (ng/ml) | 139.43 | 147.01 |
| $T_{max1}$ (hr) | 6.56 | 5.32 |
| $T_{max2}$ (hr) | 17.24 | 16.33 |
| $T_{max}$ (hr) | 15.80 | 10.99 |
| $K_e$ (1/hr) | 0.1319 | 0.1434 |
| $Elim_{1/2}$ (hr) | 5.47 | 5.20 |

The pharmacokinetic data for the subjects (n=7) who were fed prior to administration was as shown below in Table 6:

TABLE 6

| Parameter (fasted subjects) | Example 1 Diltiazem Capsule Formulation | CARDIZEM ® CD Capsule Formulation |
|---|---|---|
| $AUC_{0-48}$ (ng-hr/ml) | 3146.01 | 3040.75 |
| $AUC_{inf}$ (ng-hr/ml) | 3217.37 | 3109.78 |
| $C_{max1}$ (ng/ml) | 108.86 | 114.13 |
| $C_{max2}$ (ng/ml) | 157.49 | 147.39 |
| $C_{max}$ (ng/ml) | 157.49 | 151.57 |
| $T_{max1}$ (hr) | 6.67 | 7.04 |
| $T_{max2}$ (hr) | 18.79 | 20.13 |
| $T_{max}$ (hr) | 18.79 | 17.63 |
| $K_e$ (1/hr) | 0.1394 | 0.1336 |
| $Elim_{1/2}$ (hr) | 5.01 | 5.47 |

As can be seen from FIGS. 2 and 3, for both the Example 1 diltiazem capsule formulation and for the CARDIZEM® CD capsule formulation, there are two peak concentrations, $C_{max1}$ and $C_{max2}$, which occur at times $T_{max1}$ and $T_{max2}$, respectively. The value for $C_{max}$ refers to the least square means of the overall peak concentration and the value for $T_{max}$ refers to the least square means of the time to reach the maximum concentration. The $K_e$ values are the apparent first order elimination rate constants which relate to the rate at which the drug is metabolized or excreted. The value for $Elim_{1/2}$ calculated as $0.693/K$ indicates the time required to reduce the concentration by 50%.

It will be observed that the pharmacokinetic data for the Example 1 diltiazem capsule formulation and for the CARDIZEM® CD capsule formulation are very similar even though the Example 1 diltiazem capsule formulation does not employ an organic acid or a multi-layer coating.

Thus, while there have been shown and described and pointed out fundamental novel features of the invention as applied to a preferred embodiment thereof, it will be understood that various omissions and substitutions and changes in the form and details of the disclosed invention, may be made by those skilled in the art without departing from the spirit of the invention. It is the intention, therefore, to be limited only as indicated by the scope of the claims appended hereto.

What is claimed is:

1. A once-a-day controlled absorption diltiazem pellet formulation for oral administration comprising a blend of long lag and short lag pellets, each of said pellets comprising:
    (a) a core comprising 18% to 34% sugar spheres, 60% to 80% diltiazem hydrochloride and 2% to 6% hydroxypropylcellulose, expressed as percentages of the total weight of the core, said core being substantially free of organic acid, the amount of any such organic acid being sufficiently small so as not to substantially affect the release rate of diltiazem hydrochloride from the core, and
    (b) a single coating layer having a thickness surrounding said core, each coating layer consisting essentially of 31% to 35% talc, not more than 8% sodium lauryl sulfate, not more than 8% triethyl citrate, 2% to 7% of a first copolymer of acrylic and methacrylic acid esters, and 53% to 59% of a second copolymer of acrylic and methacrylic acid esters, expressed as percentages of the total weight of the coating layer, the first copolymer being permeable to water and diltiazem, the second copolymer being less permeable to water and diltiazem than said first copolymer, the thickness of the coating layer surrounding the long lag pellet core being greater than the thickness of the coating layer surrounding the short lag pellet core such that the diltiazem from the core of the short lag pellets is released before the diltiazem from the core of the long lag pellets, the thicknesses of said coating layers of said short and long lag pellets being effective to permit the release of a therapeutically effective amount of said diltiazem from said pellet formulation at a rate allowing controlled absorption thereof over, on the average, a twenty-four hour period following oral administration, said rate being measured in vitro as a dissolution rate of said pellets, which when measured in a type 2 dissolution apparatus (paddle) according to the U.S. Pharmacopoeia XXII in 0.1N HCl at 100 rpm substantially corresponds to the following dissolution pattern:
        a) not more that 10% of the total diltiazem is released after 1 hour of measurement in said apparatus;
        b) from 20% to 45% of the total diltiazem is released after 6 hours of measurement in said apparatus;
        c) from 35% to 45% of the total diltiazem is released after 8 hours of measurement in said apparatus;
        d) from 35% to 45% of the total diltiazem is released after 11 hours of measurement in said apparatus;
        e) not less than 85% of the total diltiazem is released after 18 hours of measurement in said apparatus; and
        f) not less than 90% of the total diltiazem is released after 24 hours of measurement in said apparatus.

2. The diltiazem pellet formulation of claim 1, wherein said short lag pellets, when measured in a type 2 dissolution apparatus (paddle) according to the U.S. Pharmacopoeia XXII in 0.1N HCl at 100 rpm, exhibit the following in vitro dissolution profile: not more than 10% of the total diltiazem is released after 1 hour, 50% of the total diltiazem is released between 3 and 4½ hours, and not less than 85 % of the total diltiazem is released after 8 hours; and said long lag pellets, when measured in a type 2 dissolution apparatus (paddle) according to the U.S. Pharmacopoeia XXIII in 0.1N HCl at 100 rpm, exhibit the following in vitro dissolution profile: not more than 5% of the total diltiazem is released after 1 hour, 50% of the total diltiazem is released between 12 and 16 hours, and not less than 85 % of the total diltiazem is released after 18 hours.

3. The pellet formulation of claim 1, wherein the core further comprises at least one of a dispersing agent, a glidant and a surfactant.

4. The pellet formulation of claim 2, wherein the core further comprises at least one of a dispersing agent, a glidant and a surfactant.

5. A capsule or tablet formulation comprising pellets according to claim 1.

6. A capsule or tablet formulation comprising pellets according to claim 2.

* * * * *